(12) United States Patent
Balogh et al.

(10) Patent No.: US 8,935,106 B2
(45) Date of Patent: Jan. 13, 2015

(54) PIPELINE HYDROSTATIC TESTING DEVICE

(75) Inventors: John A. Balogh, Seven Hills, OH (US); David L. Thomas, Strongsville, OH (US)

(73) Assignee: Adalet/Scott Fetzer Company, Cleveland, OH (US)

( * ) Notice: Subject to any disclaimer, the term of this patent is extended or adjusted under 35 U.S.C. 154(b) by 617 days.

(21) Appl. No.: 13/283,799

(22) Filed: Oct. 28, 2011

(65) Prior Publication Data
US 2013/0110417 A1    May 2, 2013

(51) Int. Cl.
| | | |
|---|---|---|
| G06F 19/00 | (2011.01) | |
| G01M 3/28 | (2006.01) | |
| G01N 3/12 | (2006.01) | |

(52) U.S. Cl.
CPC ............. G01M 3/2846 (2013.01); G01N 3/12 (2013.01)
USPC .......................................................... 702/47

(58) Field of Classification Search
USPC .......................................................... 702/47
See application file for complete search history.

(56) References Cited

U.S. PATENT DOCUMENTS

| | | | | |
|---|---|---|---|---|
| 3,889,466 A | * | 6/1975 | Castela et al. ................. 60/533 |
| 4,480,901 A | * | 11/1984 | Osegowitsch et al. ........ 396/617 |
| 4,546,649 A | * | 10/1985 | Kantor ............................ 73/168 |
| 5,161,954 A | * | 11/1992 | Matheson et al. ............. 417/12 |
| 5,302,090 A | * | 4/1994 | Schoo ........................... 417/379 |
| 5,538,276 A | * | 7/1996 | Tullis ....................... 280/124.158 |
| 5,540,049 A | * | 7/1996 | Lunzman ......................... 60/327 |
| 5,980,102 A | * | 11/1999 | Stulen et al. ..................... 374/45 |
| 6,196,316 B1 | * | 3/2001 | Bosma et al. ................. 166/294 |
| 6,484,816 B1 | * | 11/2002 | Koederitz ......................... 175/25 |
| 7,066,010 B2 | | 6/2006 | Bryant et al. |
| 7,380,453 B1 | * | 6/2008 | Van Every et al. ......... 73/170.29 |
| 7,409,852 B2 | | 8/2008 | Herzog et al. |
| 2003/0167919 A1 | * | 9/2003 | Schempf ........................... 95/15 |
| 2004/0109800 A1 | * | 6/2004 | Pahlman et al. .............. 423/210 |
| 2005/0077049 A1 | * | 4/2005 | Moe et al. ..................... 166/355 |
| 2005/0235745 A1 | * | 10/2005 | Proett et al. ................ 73/152.22 |
| 2005/0252278 A1 | * | 11/2005 | Bryant et al. .................. 73/49.5 |
| 2005/0274511 A1 | * | 12/2005 | Collins et al. ............. 166/254.2 |
| 2005/0274518 A1 | * | 12/2005 | Collins et al. ................ 166/285 |
| 2006/0004492 A1 | * | 1/2006 | Terlson et al. ................ 700/276 |
| 2007/0288160 A1 | * | 12/2007 | Ebert ............................. 701/207 |
| 2008/0010232 A1 | * | 1/2008 | Kant et al. ...................... 706/52 |
| 2008/0202358 A1 | * | 8/2008 | Backhaus ........................ 100/43 |
| 2009/0112525 A1 | * | 4/2009 | Adani ............................ 702/189 |
| 2010/0089126 A1 | * | 4/2010 | Sweeney .......................... 73/40 |
| 2010/0126727 A1 | * | 5/2010 | Vinegar et al. ................ 166/302 |
| 2010/0324835 A1 | * | 12/2010 | Fox et al. ......................... 702/33 |
| 2011/0178736 A1 | * | 7/2011 | Westra et al. ................... 702/50 |
| 2012/0079880 A1 | * | 4/2012 | Freitag ............................. 73/198 |

\* cited by examiner

Primary Examiner — Jonathan C Teixeira Moffat
Assistant Examiner — Alvaro Fortich
(74) Attorney, Agent, or Firm — Jones Day

(57) ABSTRACT

A portable test apparatus is for performing a pressure test of a vessel into which a liquid is being forced by a pump. The test apparatus includes a pressure sensor configured to measure pressure in the vessel. A processor is configured to monitor, during the test, stroke counts communicated from the pump and the pressure sensed by the pressure sensor. A graphical user interface includes input fields to receive user-input of test parameter information, and further includes a graphical representation of the stroke counts and measured pressure in real time during the test.

15 Claims, 14 Drawing Sheets

| Time | Pressure | Ambient Temp | Pipeline Temp | Stroke Count | Notes |
|---|---|---|---|---|---|
| 9:05:24 AM | 1279 | 69 | 64 | 1451 | |
| 9:18:31 AM | 1386 | 69 | 64 | 1693 | |
| 9:30:58 AM | 1460 | 69 | 64 | 1793 | PLeak test |
| 9:35:50 AM | 1460 | 69 | 64 | 1793 | |
| 9:40:47 AM | 1460 | 69 | 65 | 1793 | |
| 9:45:08 AM | 1460 | 69 | 65 | 1793 | |
| 9:45:24 AM | 1568 | 69 | 67 | 2071 | Start stroke |
| 9:56:39 AM | 1658 | 69 | 67 | 2283 | |
| 10:05:11 AM | 1745 | 69 | 68 | 2594 | |
| 10:14:24 AM | 1830 | 69 | 68 | 2861 | |
| 10:25:30 AM | 1830 | 69 | 68 | 2861 | |
| 10:26:36 AM | 1830 | 69 | 69 | 2861 | |
| 10:27:35 AM | 1830 | 69 | 69 | 2861 | Start 8 hour |

PTest: 1830 PSI
PTest High Limit: 1831 PSI
PTest Low Limit: 1816 PSI
Ambient Temp: 69 Deg F
Pipeline Temp: 69 Deg F

PIPELINE HYDROSTATIC TESTING DEVICE

TECHNICAL FIELD

This application relates to hydrostatic pressure testing of vessels, such as pipelines.

BACKGROUND

A hydrostatic pressure test is used to assess the integrity of a vessel, such as a pipe. The vessel can, for example, be a section of a pipeline that has been cut from the remainder of the pipeline or a pipe that is to be added to a pipeline. The pipe is capped at both ends and filled with liquid pressurizing media. During the test, a pump incrementally forces an additional volume of media into the pipe with each stroke of the pump's piston. The pipe's internal pressure is monitored and provides an indication of a leak or other indication of lack of pipe integrity.

SUMMARY

A portable test apparatus is for performing a pressure test on a vessel. During the test, an additional amount of liquid is forced into the vessel by each successive stroke of a pump. The test apparatus includes a pressure sensor configured to measure pressure in the vessel. A processor monitors, during the test, the strokes communicated from the pump and the pressure sensed by the pressure sensor. A graphical user interface includes input fields to receive user-entered test parameter information, and further includes a graphical representation of the stroke counts and measured pressure in real time during the test.

The stroke counts and pressure may be secured from modification during the test. The user-entered test parameter information can include elevations relative to sea level at different locations along vessel. The test apparatus can further include a temperature sensor for measuring temperature, for the processor to monitor the temperature measured by the temperature sensor. The vessel can be a pipe. The processor saves a secure report of data collected in the test in a data file in an electronic data storage medium.

BRIEF DESCRIPTION OF THE DRAWINGS

FIGS. 4-12 are screen shots of user interface display screens (windows) provided by the computer for performing the test.

DETAILED DESCRIPTION

Figure 1:
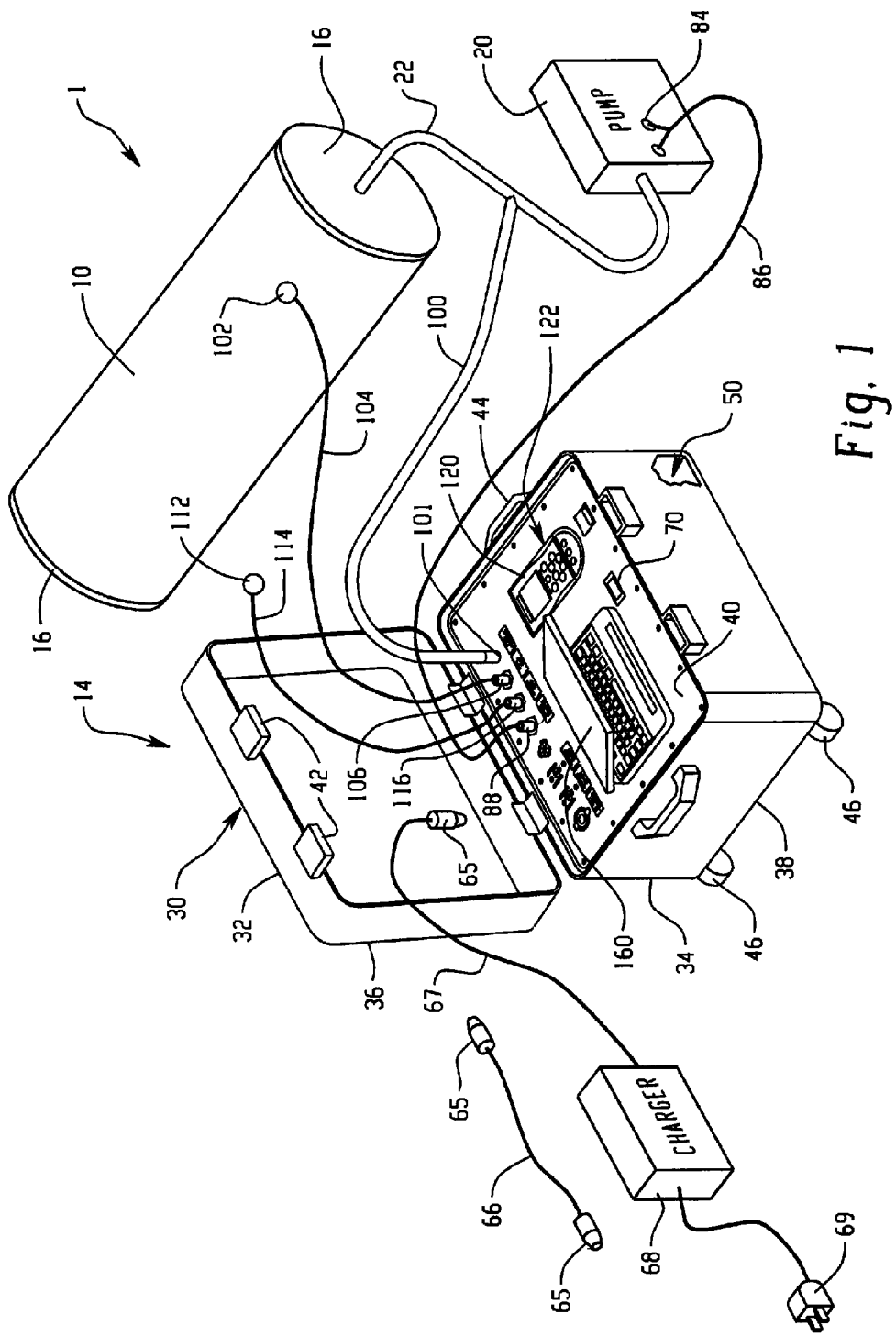
FIG. 1 is a perspective view of a pipe to be tested and a test apparatus for performing the test, the test apparatus including a console and a computer.

The apparatus shown in the figures has parts that are examples of the elements recited in the claims. The apparatus thus includes examples of how a person of ordinary skill in the art can make and use the claimed invention. They are described here to meet the requirements of enablement and best mode without imposing limitations that are not recited in the claims As shown in FIG. 1, the apparatus 1 includes a vessel, in this case a pipe 10 that is a pipe section isolated from, such as by being cut from, a pipeline. A test equipment 14 is used to perform a hydrostatic pressure test to check the pipe 10 for integrity and breaches (leaks). In the test, the pipe 10 is sealed with caps 16 at its opposite ends and then filled with a pressurization media. The media in this example is a liquid such as water. A hydraulic pump 20 forces additional liquid into the pipe 10 through a fill tube 22. Each stroke of the pump's piston injects a uniform and known amount of water into the pipe 10, thereby uniformly and incrementally increasing the hydraulic pressure within the pipe 10 during the test. Concurrently, the test equipment 14 monitors ambient temperature and the pipe's internal pressure and temperature, and yields a table and a graph of these parameters against the volume of media that is injected into the pipe. This volume is indicated in terms of stroke count (number of pump strokes). That is because the pump injects the same volume of media into the pipe with each piston stroke, so the volume per stroke is uniform throughout the test. The graph and table are analyzed to assess the pipe's integrity. This test can be used to assess the integrity of pressure vessels for various applications including new construction, repair, replacement and reclassification (upgrade or downgrade).

The test equipment 14 includes a console 30 that has carrying-case type housing 32. The case 32 includes a base 34 and at top cover 36 that are attached together by a hinge. The base 34 has a bottom surface 38, configured to rest on a ground or table when the console 30 is being used and operated. The base 34 further includes a top surface 40 serving as a control panel. The case 32 further has latches 42 for latching the case closed. The case 32 further has a telescoping handle 44 configured to be grasped for carrying the console 30 or wheeling the console 30 by wheels 46 that are attached to the case's bottom 38. A cavity 50 of the base 32 is bounded by base's bottom and top surfaces 38, 40.

Figure 2:
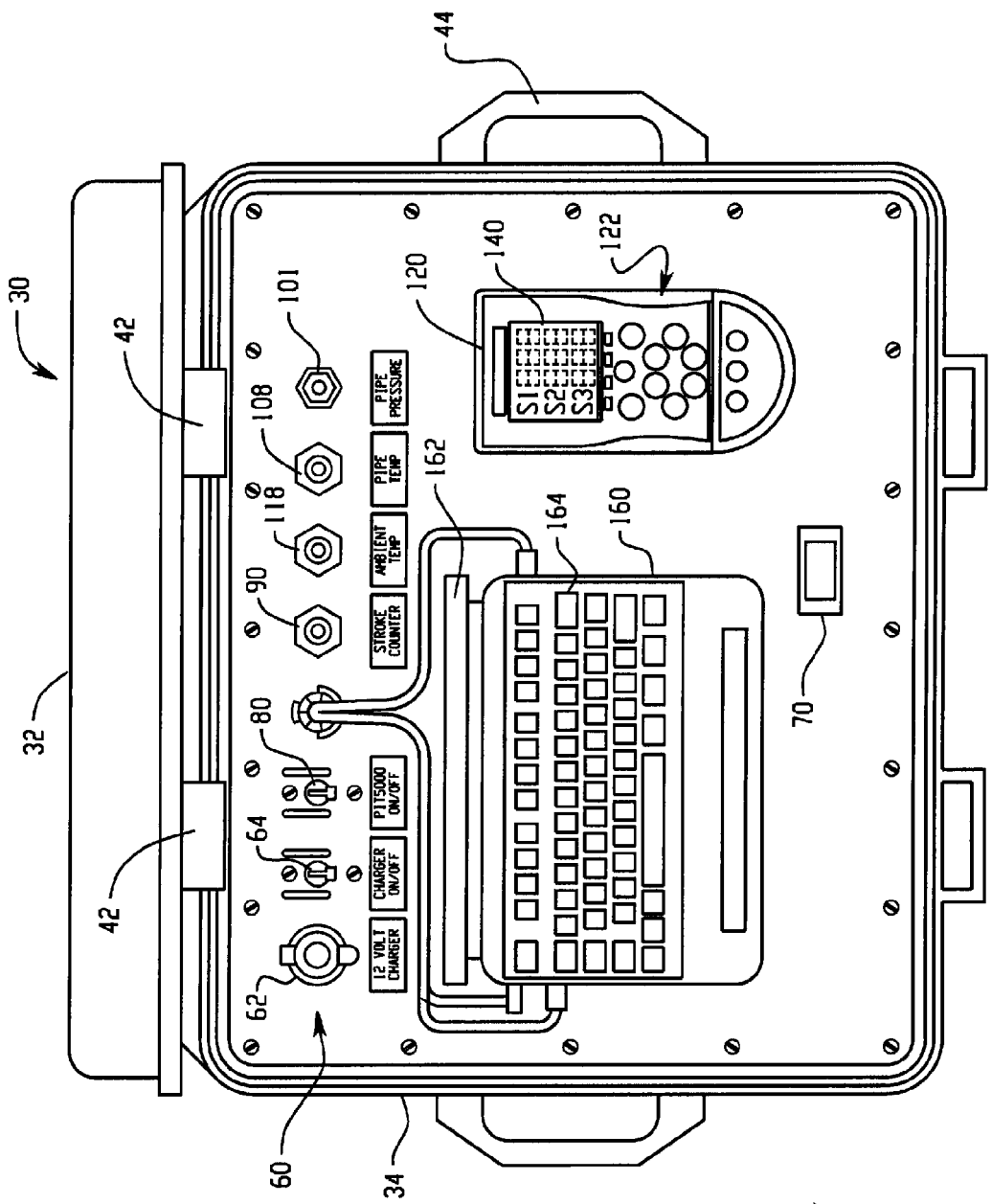
FIG. 2 is a top view of a top panel of the console.
Figure 3:
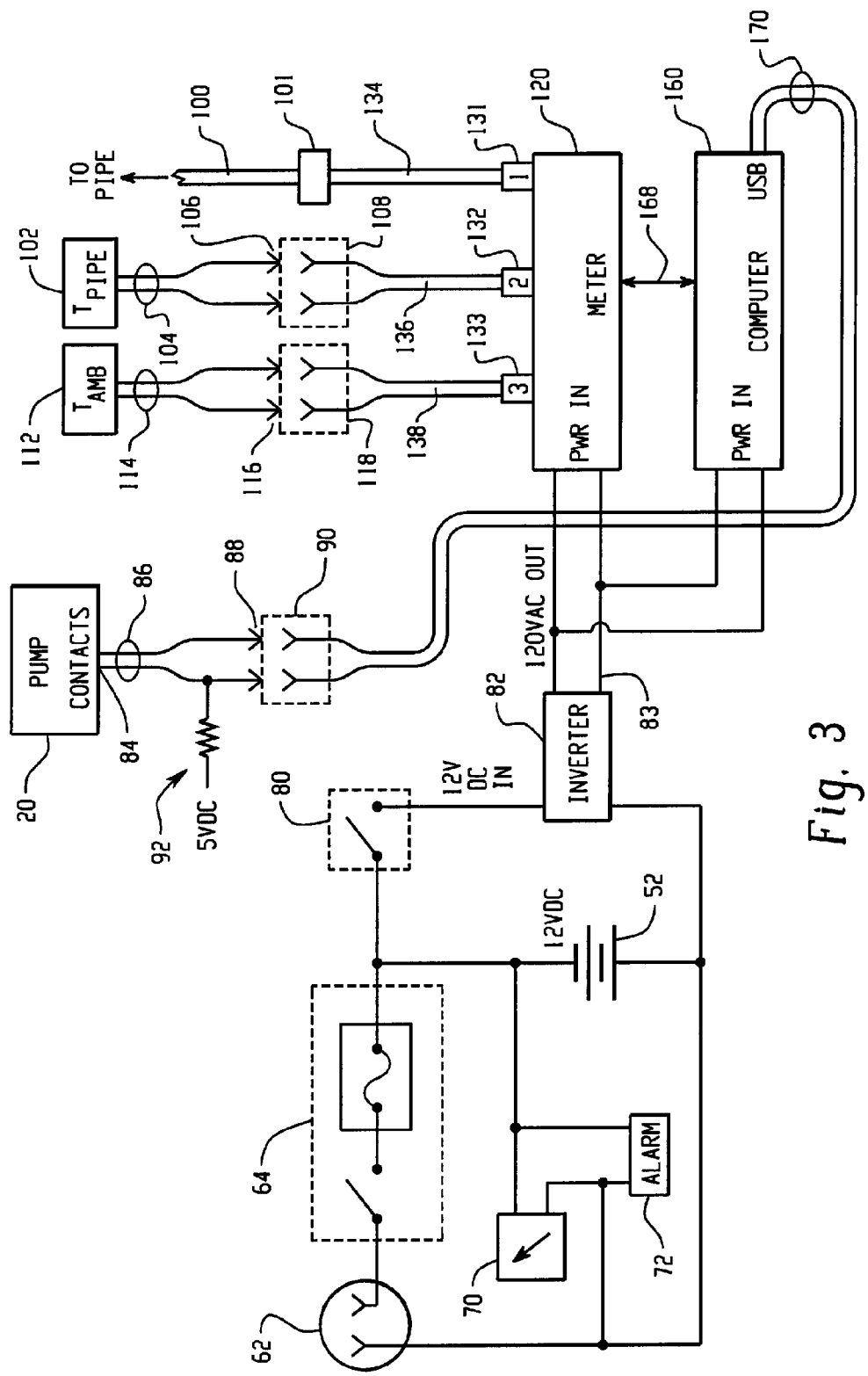
FIG. 3 is a schematic view of wiring within the console and wiring that connects the console to other components of the test apparatus.

Referring to FIGS. 2-3, the cavity 50 (FIG. 1) contains a 12-volt DC battery 52 in the cavity. The base's top surface has a strip of terminals 60, one of which is a low-voltage 12VDC input power terminal 62. This low-voltage input power terminal 62 is connected to the battery 52 via a breaker-protected "Charger ON/OFF" switch 64 located along the terminal strip 60. The low-voltage input power terminal 62 is an automotive (cigarette-lighter) style electrical socket. It is configured to receive an automotive style electrical plug 65 of either of two power cables 66, 67 (FIG. 1). One power cable 66 has, at its opposite end, an automotive style plug 65 that can be plugged into a cigarette lighter socket of a car. The other power cable 67 is the output cable of a 120VAC-to-12VDC power adapter 68 that has a wall plug 69 configured to plugged into a wall socket. A digital voltage meter 70 indicates battery strength by displaying the battery's voltage. An audible alarm device 72 in the cavity 50 will sound when the battery voltage drops below 10.5 VDC.

A main ON/OFF switch 80 along the terminal strip 60 controls electricity from the battery 52 to in inverter 82 in the cavity 50. The inverter converts the 12VDC to an 120VAC output 83.

The pump 20 has a pair of dry normally-open electrical contacts 84 that are momentarily electrically shorted by the pump upon each piston stroke of the pump. The contacts 84 are connected by a two-wire cable 86 to a plug 88 that is inserted into a "stroke count" electrical socket terminal 90 along the terminal strip 60. A biasing device 92 within the cavity 50 (FIG. 1) applies a 5VDC bias across the stroke-count cable wires 86, so that each stroke of the pump 20 is accompanied by a momentary 5-volt drop, from 5V to 0V, across the wires when the pump 20 shorts the wires 86.

A hose 100 (flexible tubing) communicates the pipe's internal pressure to a pressure port 101 along the terminal strip 60. A pipe temperature sensor 102, in this case an RTD (resistive temperature device) is adhered to the pipe 10. The RTD is connected by a two-wire cable 104 to a plug 106 that is inserted into a "pipe temperature" electrical socket terminal 108 along the along the terminal strip 60. An ambient temperature sensor 112, in this case an RTD, is exposed to the ambient air. It is connected by a two-wire cable 114 to a plug 116 that is inserted into an "ambient temperature" electrical terminal socket 118 along the terminal strip 60.

A multifunction meter 120 is seated in a pocket 122 of the control panel 40. The meter 120 is powered by the 12VDC-to-120VAC inverter's output cable 83. The meter 120 has three bays into which are removably installed a pressure sensor module 131 and first and second temperature sensor modules 132, 133. In the cavity 50 (FIG. 1), a hose 134 couples the pressure port 101 to the pressure sensor module 131. Two cables 136, 138 couple the pipe-temperature and ambient-temperature terminals 108, 118 respectively to the temperature sensor modules 132, 133. The pressure sensor module 131 includes a pressure sensor that provides the meter 120 with an electrical signal whose voltage or current is a function of the hydrostatic pressure of the liquid in the pipe. Each temperature sensor module 132, 133 provides an activation voltage to the respective RTD and provides the meter 120 with a voltage-based or current-based electrical signal that is a function of the respective measured temperature. The meter 120 displays the resulting pressure and temperature readings on its LCD-display 140. The meter 120 also communicates the pressure and temperature readings through a data communication port, in this case a DB-9 RS232 serial port.

A laptop computer 160 rests on, and is secured to, the control panel 40. It is powered by a cable from the inverter's 120VAC output 83. The computer 160 has a processor that executes the software functions performed by the computer. The computer 160 also has a display 162. It also has one or more input devices, such as a keyboard 164 and a mouse, a mouse pad and/or touch-screen configuration. A communication cable 168 conveys data, including the pressure and temperature readings, from the meter's communication port to a USB input of the computer. Another cable 170 couples the stroke count terminal 90 to another USB input of the computer 160.

The computer 160 includes software programming instructions, which can be based on LabVIEW™ platform and development environment. The software is executed by the computer's processor to graph the measured pipe pressure, pipe temperature and ambient temperature against time of day on the display 162, and to graph the measured pipe pressure against stroke count on the display 162, and to provide over-range notifications on the display 162. The computer controller starts counting the pump strokes once the "Stroke Start Pressure" 508 is reached, and also counts and logs the pump strokes required to generate each user-selected pressure increment 510 (in this case 10 PSI) until the pipe's internal pressure (PTest Instrument Pressure) is achieved.

The computer's software program provides a graphic user interface (GUI) based on tabs. Some tabs have different sub-tabs. And each tab or sub-tab is selected with one of the computer's input devices 164 to call up a corresponding display screen (window). A screen shot for each sub-tab is shown in a respective figure of FIGS. 4-12. In this example, "PIT5000" is the model name of the console 30 and "MFT4000" is the model name of the multifunction meter 120.

Figure 4:
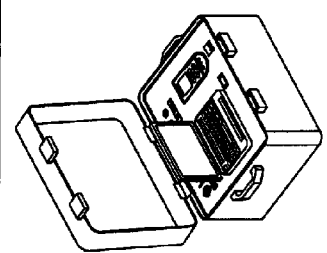

As shown in FIG. 4, the first tab is "Setup" 400. Its sub-tabs are "Test Info", "Pump Info", "Site Info", "Test Limits", "PC Setup", and "Manual".

Figure 9:
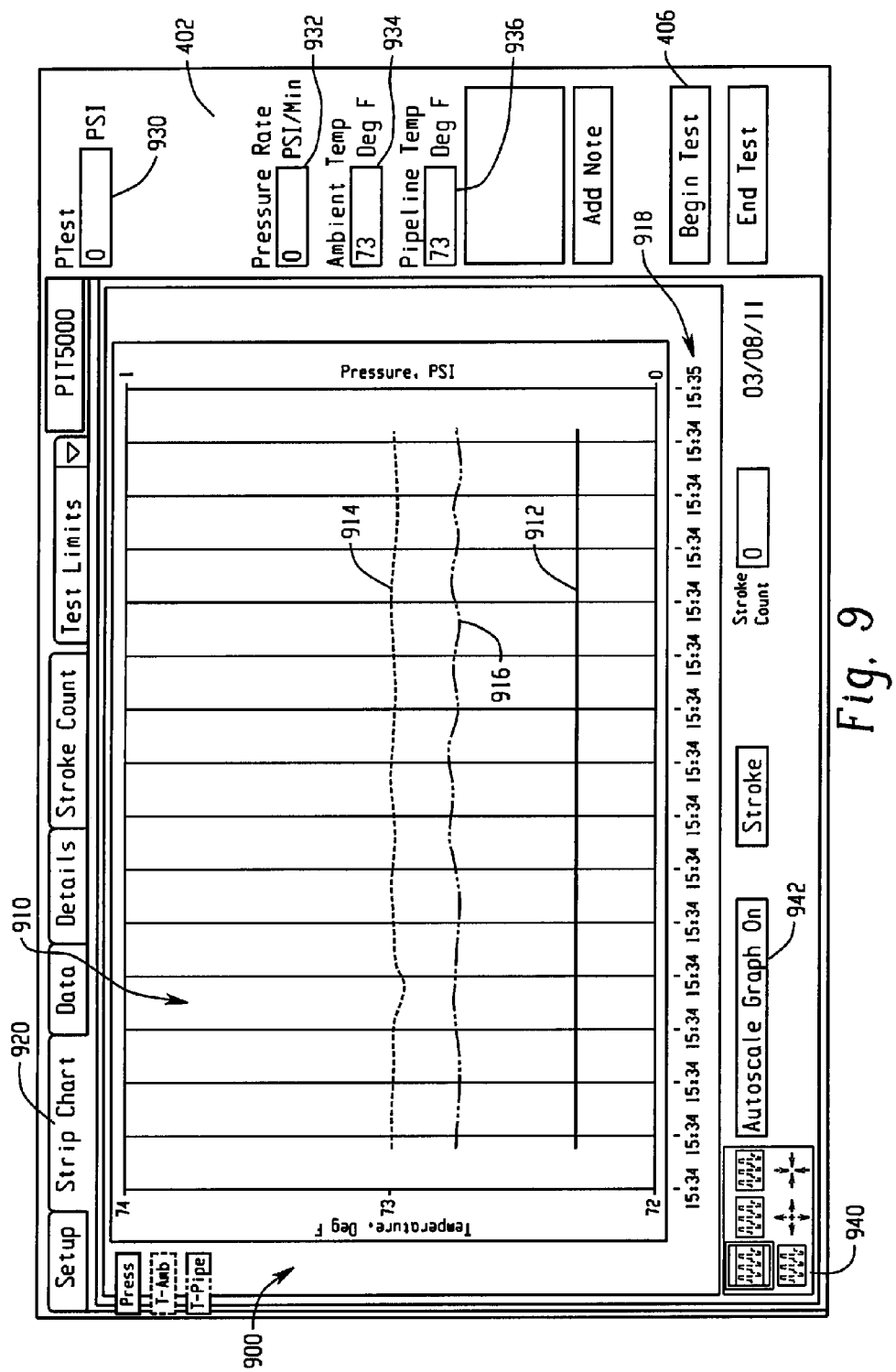

A data panel 402 (or side panel) is shown at the right hand side of all tabs after Setup information is entered and a "Start Program" soft button 404 is selected. Certain test data is displayed in the side panel 402. Visual alarms (warnings) are also displayed in this area, and can be indicated by a red flashing background for the corresponding GUI window. The side panel 402 has soft buttons. The buttons vary with test progress. For example, a user clicks the "Start Program" button in the side panel 402 to cause the computer 160 to start a live plot on the "Strip Chart" tab screen (FIG. 9) and to begin logging data to the computer's data storage medium, such as a hard drive. Once the "Start Program" button 404 is selected, the "Start Program" button changes to a "Begin Test" button 406 (FIG. 9). Once pressure reaches PTest Instrument Pressure 724, the test pipe is capped off and the operator is ready to begin the test period. The "Begin Test" button is selected to monitor and record pressure and temperature during the test period. Pressing an "End Test" button 408 ends the test at any time. The "End Test" button 408 ends the current test after a user confirmation step, and completes the data log for the session. To continue documenting a test after "End Test" 408 is selected and confirmed, the user may start a new program and use a different file name to record any remaining testing on the hard drive.

Most "Setup" sub-tabs prompt for alpha or numeric data entry to document site information, design parameters, test limits or notes to be integrated in a data log set. Information is added or edited by clicking on a desired field and typing as needed. Standard text editing features are supported. Alternatively, the user can click on an up arrow or down arrow to increment or decrement the displayed value. Drop down menu boxes are used for some data entries. In these cases, a user clicks the down arrow and then clicks on the desired menu item to select. All Setup sub-tabs should be completed prior to starting a test program. All edited information under the Setup tab is locked out by the computer once the "Start Program" button is selected but the information will remain viewable. The data entered by the user and the stroke counts and pressure being monitored and stored are secure from modification during the test.

In FIG. 4, the "Test Info" sub-tab 420 is selected to input information such as test name 438, operator name, site location, test media, work order number, etc. This tab 420 is also used to customize the test with different units of measure 430, data save intervals 434 and which temperature (ambient and/or pipe) to monitor and record. The user-entry in a "Test Name" field 438 is included in a file name for the stored test data. For example, where "2011-MontRelay-002" is entered in the "Test Name" field, test data would be saved to both C://console20/Data/2011-MontRelay-002_MMD-DYYYY.csv and C://console 20/Data/2011-MontRelay-002_MMDDYYYY.xls. The computer 160 will automatically save the test data to a comma-delimited file every minute during the test. The processor thus saves a secure report of the data collected in the test in a data file of the hard drive type electronic data storage medium.

A "T-pipe Required" button 440 is set to ON with green background by program default, to require the pipe temperature (Tpipe) to be plotted and recorded during the test. It can be toggled to OFF, to read "Tpipe Not Required" with red background, by the user for only the ambient temperature (Tambient) to be plotted and recorded.

The factory default is for the computer 160 to log (record) data sets in one minute intervals. That is why, in FIG. 4, a "1" appears in the "Data Save Interval" field 434. To reduce the number of data sets provided in the final report, the "Data Save Interval" field is set, using the up and down arrows, to the desired value in minutes. For example, "5" in this field will cause one data set to be logged to the computer's hard drive data storage medium every 5 minutes. However, data is saved each minute from the time "Start Program" is selected until "Begin Test" is selected regardless of this setting. The Data Save Interval (field 434) determines the data both stored and plotted after "Begin Test" is selected. That is because Data Save Interval regulates only the data saved after "Begin Test" is selected.

Engineering units of measure to be used in display screens and during the test are selected using the drop down menus for entry fields for "Pressure" 450, "Temperature" 452 and "Length" 454. The following units can be available: For Pressure: PSI, kg/cm$^2$, Bar, kPa; For Temperature: deg F, deg C; For Length: feet, meters; For Stroke Volume: gallons, liters. The computer 160 will use the user-selected units in recording and plotting data. The computer 160 may also communicate these units to the meter 120 via the serial connection so that the meter 120 can use these units when the meter displays the pressure and temperature through its own display.

Figure 5:
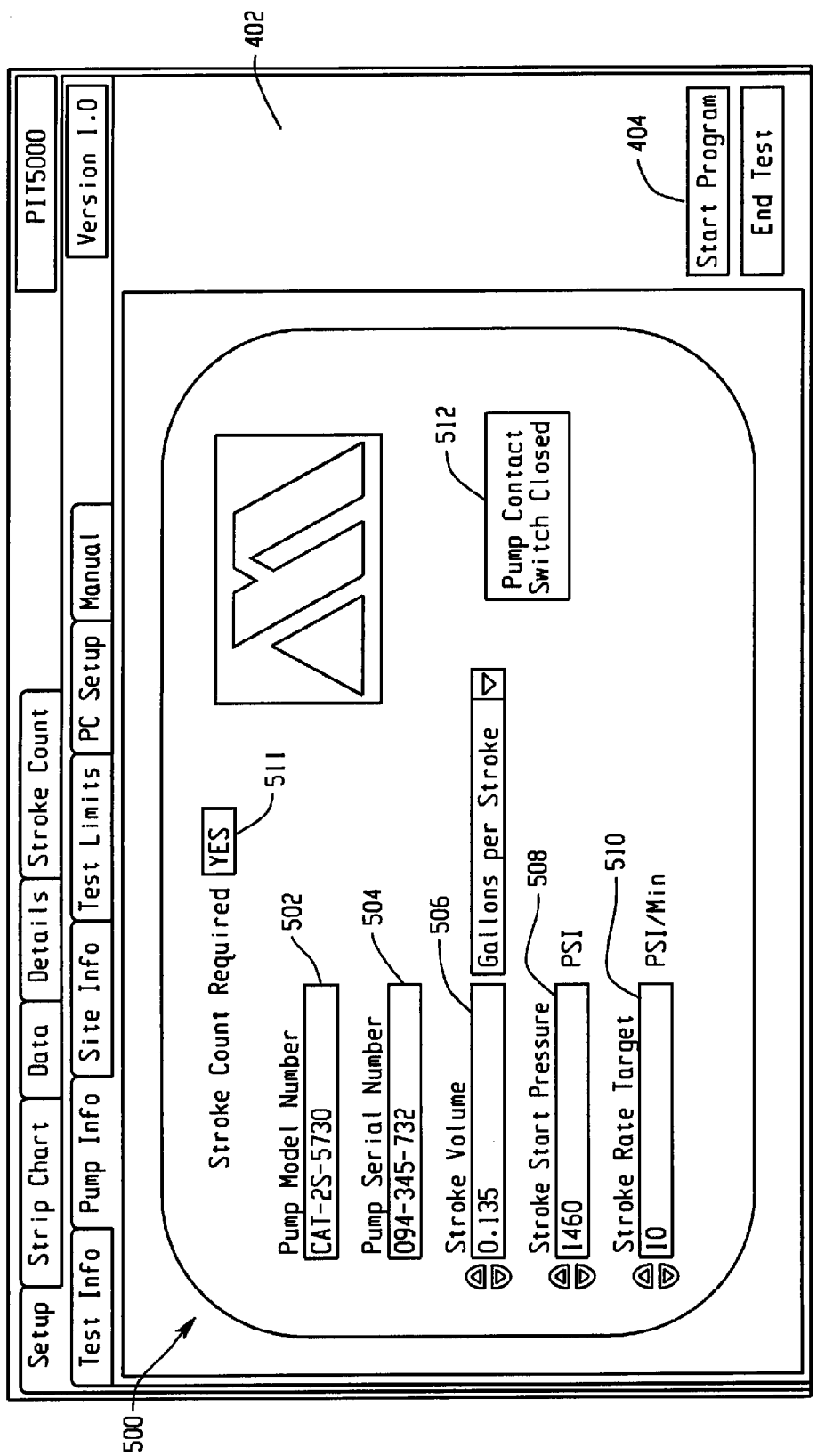

As shown in FIG. 5, a "Pump Info" sub-tab screen 500 is used to input pressure pump information in a "Pump Model Number" field 502, a "Pump Serial Number" field 504, "Stroke Volume" field 506 (volume per stroke, to enable the computer 160 to calculate and display the total liquid volume added to the pipe during the test), a "Stroke Start Pressure" field 508 (pressure to be reached to prompt the processor to start counting strokes) and a "Stroke Rate Target" field 510. Strip chart, Data, Details and Stroke Count are activated on "Start Program". The "Test Time" (702) commences with "Begin Test". After "Stroke Start Pressure" is achieved, the Stroke Count tab counts strokes every "Stroke Rate Target" value. A "Stroke-Count Required" button is clicked for its field 511 to display "YES" if a stroke count is to be used in the test, and clicked again to display "NO" if not.

A "Pump Contact Switch" box 512 is for testing the stroke counter circuit prior to starting the program. It reads "Pump Contact Switch Closed" with green background if the pump contacts are currently shorted, and reads "Pump Contact Switch Open" with red background if the contacts are not currently shorted.

Figure 6:
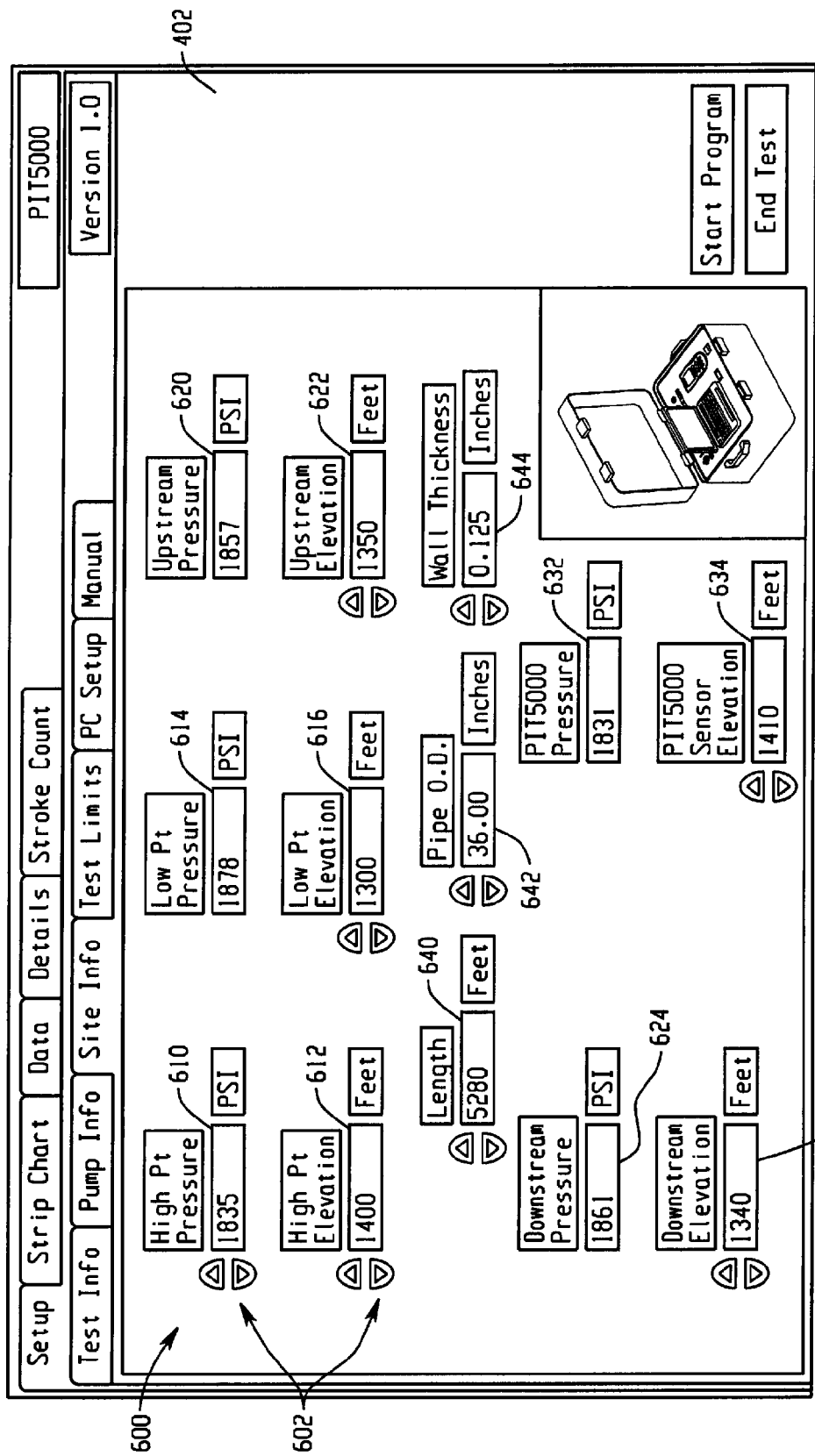

In FIG. 6, a "Site Info" sub-tab screen 600 has up and down arrows 602 to enter a variety of test parameter data. These include a "High Point Pressure" field 610 (pressure at highest location along the length of the pipe), a "High Point Elevation" field 612, a "Low Point Elevation" field 616, an "Upstream Elevation" field 622 (feet above sea level at highest end of pipe), a "Downstream Elevation" field 626 (feet above sea level at lowest end of pipe), a console sensor elevation ("PIT5000 Sensor Elevation") field 634, a pipe length field 640, a Pipe O.D. field 642 and a pipe Wall Thickness field 644. From the high point pressure and elevation, and from the elevations that are entered by the user for the other locations, the computer calculates the pressures at the other locations. These include a "Low Point Pressure" field 614, an "Upstream Pressure" field 620 (pressure at highest end of pipe), and a "Downstream Pressure" field 624 (pressure at lowest end of pipe). The computer pressure $P_x$ at any location along the pipe of elevation $E_x$ is calculated by the computer from the equation $P_x = P_{HP} + (0.433 \times [E_{HP} - E_x])$, where $P_{HP}$ is the high point pressure and $E_{HP}$ is the high point elevation. A console pressure ("PIT5000 Pressure") field 632 is measured by the console.

Figure 7:
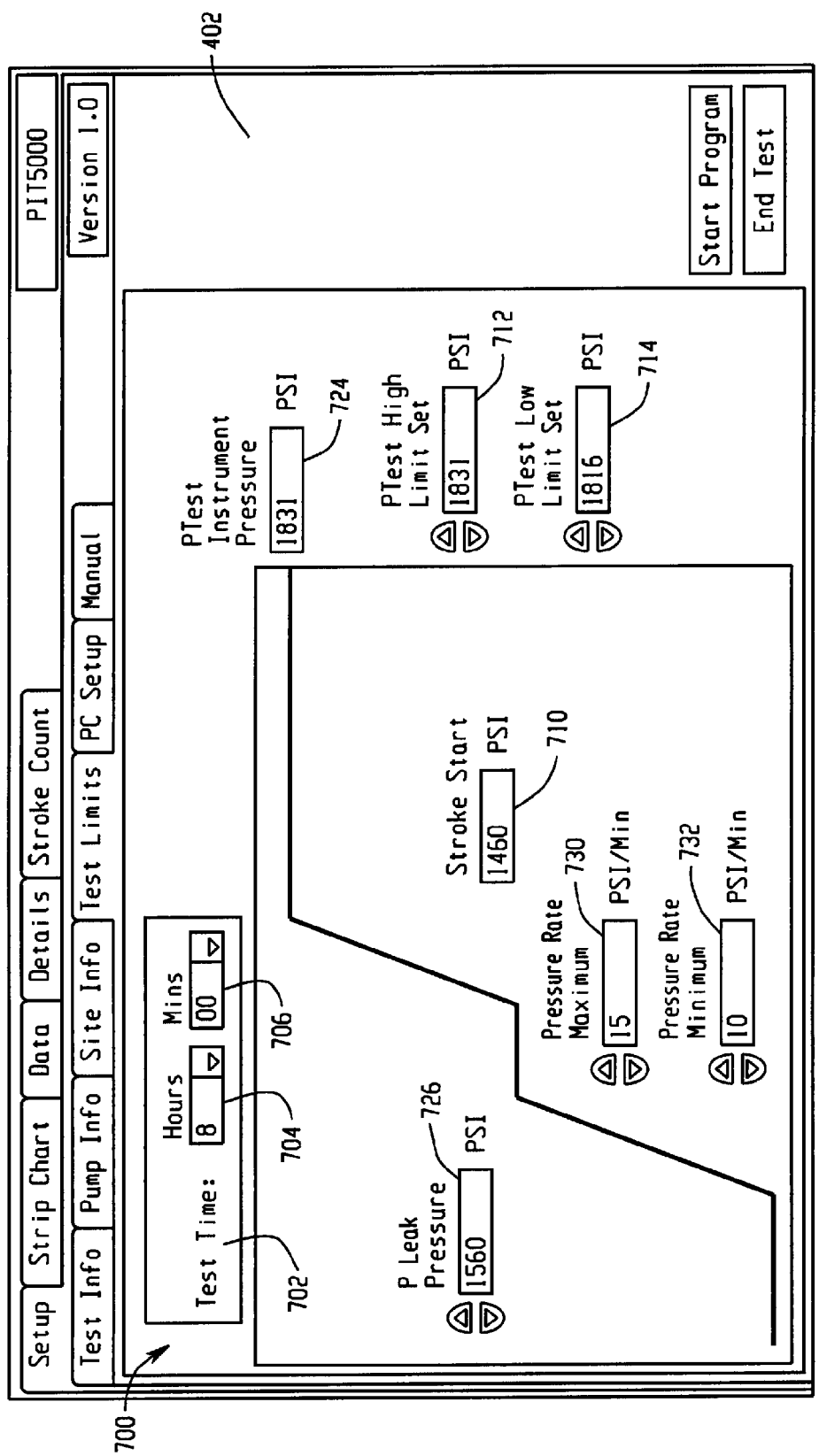

In FIG. 7, a "Test Limits" sub-tab screen 700 is used to input "Test Time" 702 in "Hours" 704 and "Minutes" 706 using drop-down menus, to be used by the computer 160 in the "Details" tab (FIG. 10). A "Stroke Start Pressure" field 710 is automatically forwarded by the computer 160 from field 508 of the "Pump Info" sub-tab (FIG. 5). The user enters values in the "PTest High Limit Set" field 712 and "PTest Low Limit Set" field 714, that are upper and lower limits for the "PTest Instrument Pressure". The "PTest Instrument Pressure" field 724 is automatically forwarded from field 632 of the "Site Info" sub-tab screen (FIG. 6). The background of the "Strip Chart" Tab's PTest field 930 may flash red if this "PTest Instrument Pressure" exceeds the "PTest High Limit Set" field. The user enters, in the "PLeak Pressure" field 726, a desired preliminary leak test pressure. A preliminary shut in hydrostatic pressure test is observed for leaks, if the user wants to check for system leaks prior to going above a pressure threshold in safety standard operating procedure. The user might perform a 15-minute leak test here, before going to higher pressures. Up and down arrows are used to enter, in the "Pressure Rate Maximum" field 730 and "Pressure Rate Minimum" field 732, maximum and minimum system pressurization rates in PSI/minute. These rates are only for triggering alarms. This sets the upper and lower alarm limits for the "Pressure Rate" field 932 in the side panel 402 of the "Strip Chart" tab screen (FIG. 9).

Figure 8:
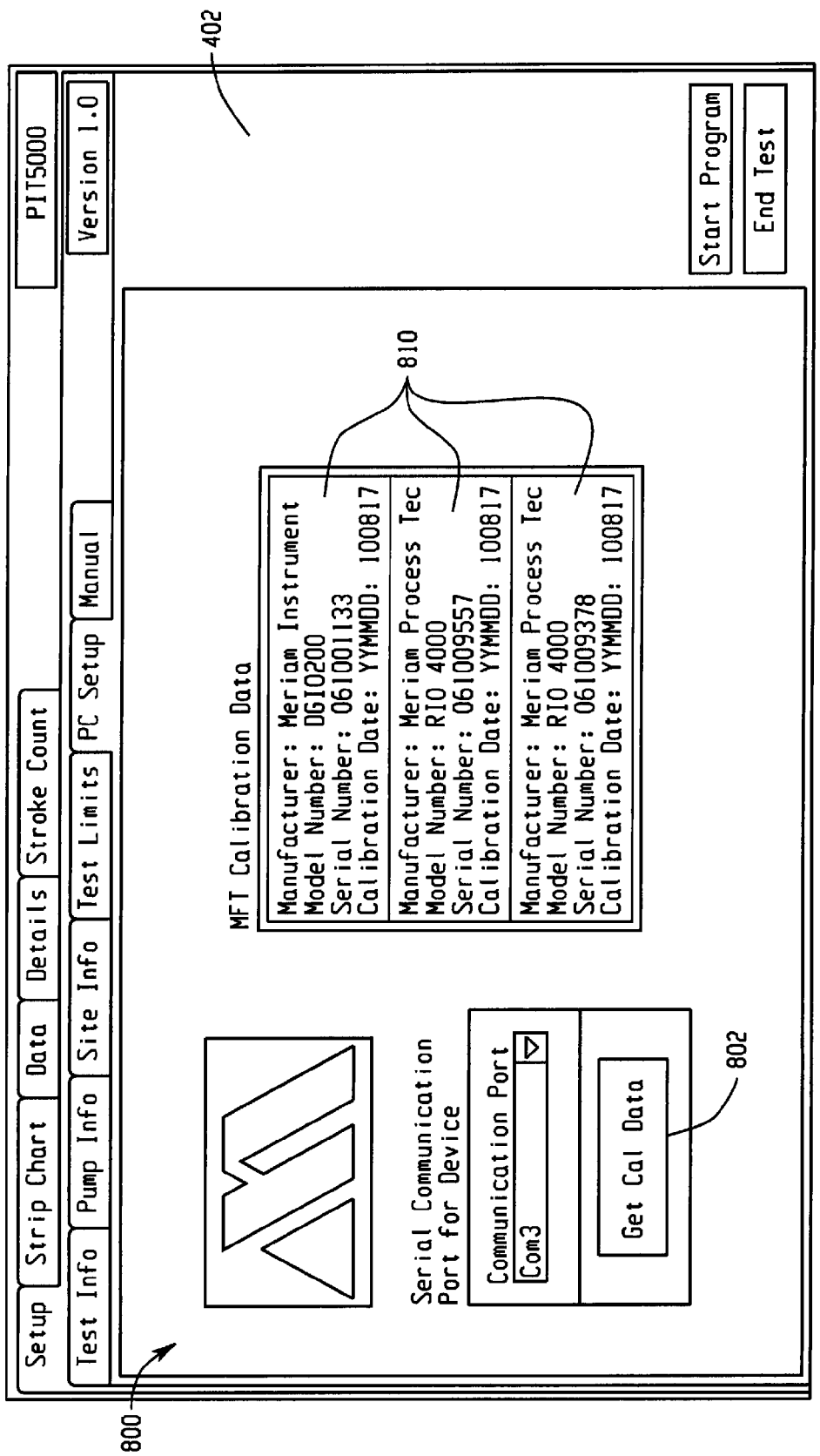

FIG. 8 shows a "PC Setup" (i.e., computer setup) sub-tab screen 800. It enables a user to click a "Get Cal Data" button 802 to verify communication with the meter 120 and to verify identification information of the measurement devices, including their serial numbers. Clicking the "Get Cal Data" button causes three "MFT" (multifunction test meter) calibration data windows 810 to populate with identification information of the modules 131, 132, 133. This is achieved by the computer 160 polling the meter 120 to retrieve the serial numbers of the three measurement modules 131, 132, 133. These serial numbers are displayed in the PC Setup screen for pretest verification when needed, and also in the Details screen for verification during the test.

A "Manual" sub-tab is clicked to access the user's manual for the test apparatus 14.

In FIG. 9, a "Strip Chart" tab screen 900 displays a live plot 910 (graph) of pipe pressure 912, Tambient (ambient temperature) 914 and Tpipe (pipe temperature) 916 versus time 918, in order to document the hydrostatic test and its duration. This screen is called up by clicking on the "Strip Chart" tab 920. It can alternatively be called up by selecting the "Start Program" button 404 from any sub-tab of the "Setup" tab 400 (FIG. 4), which then converts to a "Begin Test" button 406. The x axis is time-of-day 918 in 24-hour format. The graph's temperature axis is the left hand vertical axis, and the graph's pressure axis is the right hand vertical axis. The temperature axis is fixed to 0-150 degrees F. The pressure axis is auto-scaled throughout the test. The side panel 402 appears on the right hand side of the screen, providing the current "PTest" 930 (pipe pressure), current "Pressure Rate" 932, current "Ambient Temperature" 934, and current "Pipeline Temperature" 936. The "Begin Test" button 406 can be clicked when the PTest Instrument Pressure 724 is reached, and the shut-in 702 test period is ready to begin. Pipe pressure corresponds to the first display line "S1" of the meter 120 (FIG. 2) and is plotted against time in white. Tambient corresponds to the meter's second display line "S2" and is plotted against time in red. Tpipeline corresponds to the meter's display line "S3"

and is plotted against time in green. Display controls 940 are located in the lower left corner of the Strip Chart to manipulate viewing of the graph, such as zoom and pan. Zoom and pan can be used after the "Autoscale Graph" 942 On/Off button is set to Off. To use the zoom feature, a user clicks on a magnifying glass icon, selects the zoom icon, then moves the cursor to the graph and then left-clicks and drags to draw a box around section of interest. Or the user can select a zoom-in icon or a zoom-out icon to zoom the entire plot in or out. To use the pan feature, the user moves the cursor onto the plot, left-clicks, and holds and drags the plot as desired. The user can lock the temperature and pressure scales for consistent appearance of data over time by clicking the "Autoscale" icon to toggle it to Off.

In FIG. 10, a "Data" tab screen 1000 displays a table 1010 of data collected. Each line (row) contains a single data set comprised of time-of-day 1020 in 24-hour format, pipeline pressure 1022, ambient temperature 1024, pipeline temperature 1026, stroke count 1028 and notes 1030 for that particular time-of-day. The current pressure 1040 and the upper and lower pressure limits 1042, 1044 (imported from the "Test Limits" screen of FIG. 8) are displayed in the side panel 402 during the test. The background of field 1040 will flash red if the current pressure (in field 1040) exceeds the high limit 1042 or drops below the low limit 1044. Pressure rate is displayed in the side panel 402 during system pressurization occurring after "Start Program" button is selected and before "Begin Test" button is selected, and again after the Test Time 702 is completed. The "Add Note" button is selected to enter text that will be included in the "Notes" field for the most recent data set displayed in the most recent row of data.

Figure 11:
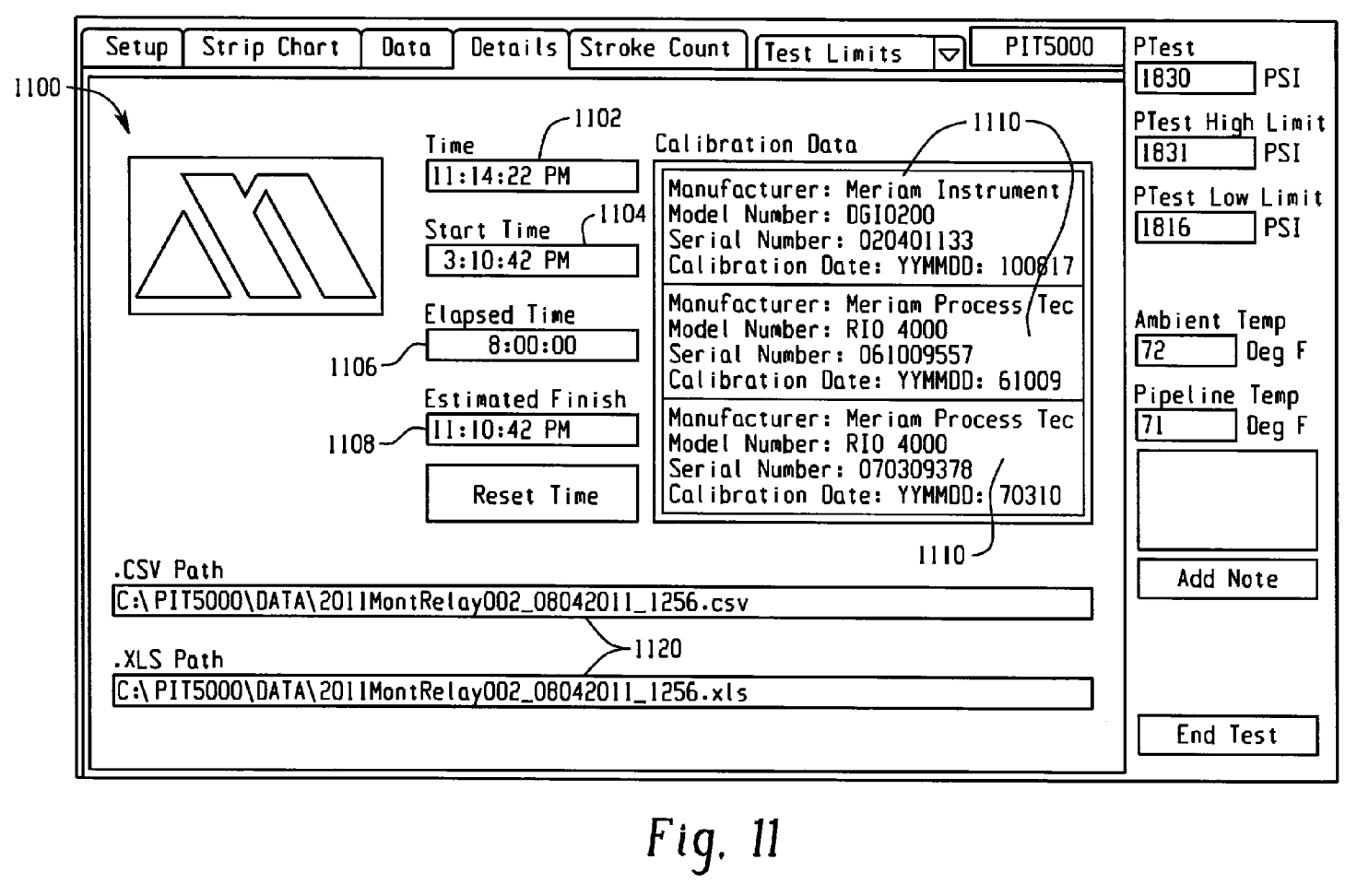

In FIG. 11, a "Details" tab screen 1100 displays basic information about the current test. This includes current time-of-day 1102, and the current test's "Start Time" 1104, "Elapsed Time" 1106 and "Estimated Finish" time 1108. This screen also displays three "Calibration Data" fields 1110 that include the manufacturer, model number, serial number and calibration date for each of the pressure sensor and two temperature sensors. This screen 1100 also displays the file locations 1120, of the computer's hard drive, where the test result files are saved. These files provide a secure electronic test report for the test. The serial numbers of the three measurement modules 131, 132, 133 are retrieved by the computer 160 from the meter 120 each time the "Details" tab is selected.

Figure 12:
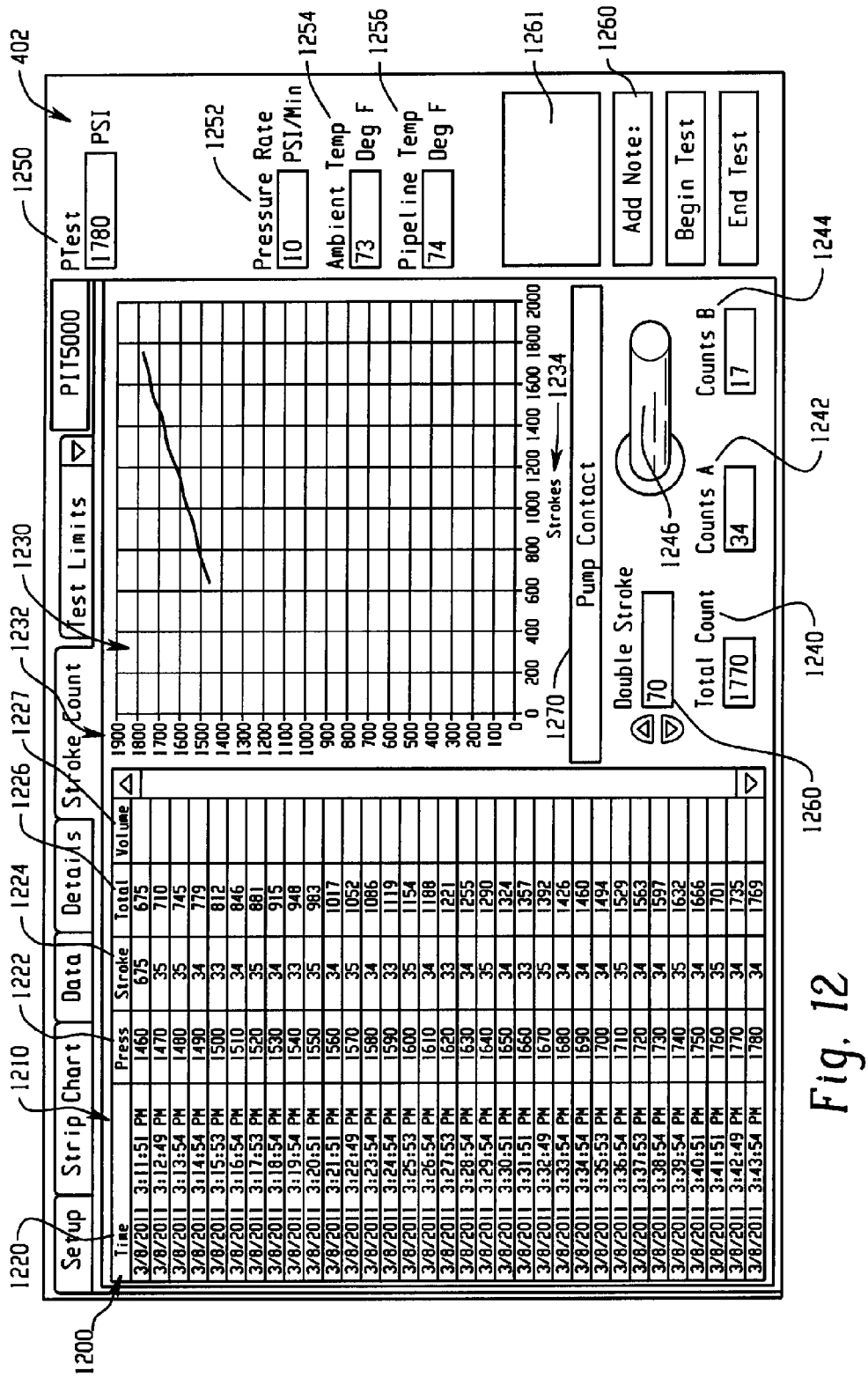

In FIG. 12, a "Stroke Count" tab screen 1200 displays a live (i.e., updated in real time) table 1210 of stroke count data. Each row of the table 1220 includes a data set for each added increment of ΔP, where ΔP (in this example 10 PSI) is the user-entered value in field 510 (FIG. 5). Each row includes, for the respective data set, time-of-day 1220 (when the data set was collected), pressure 1222, stroke subtotal 1224 (number of strokes since previous data set) and stroke total 1226 (total number of strokes since beginning of test). The most-recent data set is appended to the table in real time at the last row of the table. 1220.

The "Stroke Count" tab screen 1200 in FIG. 12 also includes a live plot 1230 of pressure 1232 vs. total number of strokes 1234. This screen also displays has a Total Count field 1240 that is continuously updated with the current total count value. Also displayed are two fields 1242, 1244 labeled "Counts A" and "Counts B". At any given time, one of them is in an active state the other is in a static state. The static field (1242 or 1244) shows the subtotal stroke count of the last recorded data set, which is displayed in the last row of the table 1240. The active field shows a continuously-updated running total of the counts collected since the last recorded data set. Once the data set being currently is recorded and added into a new row of the table, the previously active field (1242 or 1244) becomes static and freezes its value, and the previously static field becomes active and starts tallying the counts of the next data set starting from zero. A virtual toggle switch 1246 automatically points left or right to the currently active Counts field (1242 or 1244).

In FIG. 12, the side panel 402 has fields that display the current pressure 1250, pressure rate 1252, ambient temperature 1254 and pipe temperature 1256. The user can enter a threshold stroke rate value in a "Double Stroke" field 1260. A normal count is calculated as half the double stroke count. Halfway between normal stroke count and the double stroke count, at a value calculated to be 75% of the double stroke count, the background of "Pump Contact" 1270 changes from green to yellow. Normal stroke is determined from column 1224. At double stroke, the light changes to red. The user can click on the notes text entry field 1261 to type a note of up to sixty characters and then click the "Add Note" button 1260 again. The note will be merged into the data file, along with its corresponding data set, for permanent record. These notes will appear on the Data tab screen during the test in the most recent data set as soon as the Add Note button 1260 is selected. After the Start Program button is selected, the Site-Info sub-tab screen can displayed by clicking the Site-Info tab. But the Site-Info information will be grayed out and not editable after the Start Program button is selected. A "Volume" 1227 column can display total volume injected by the time of the respective data set, calculated as "Total" strokes 1226 times stroke volume 506.

Figure 13:
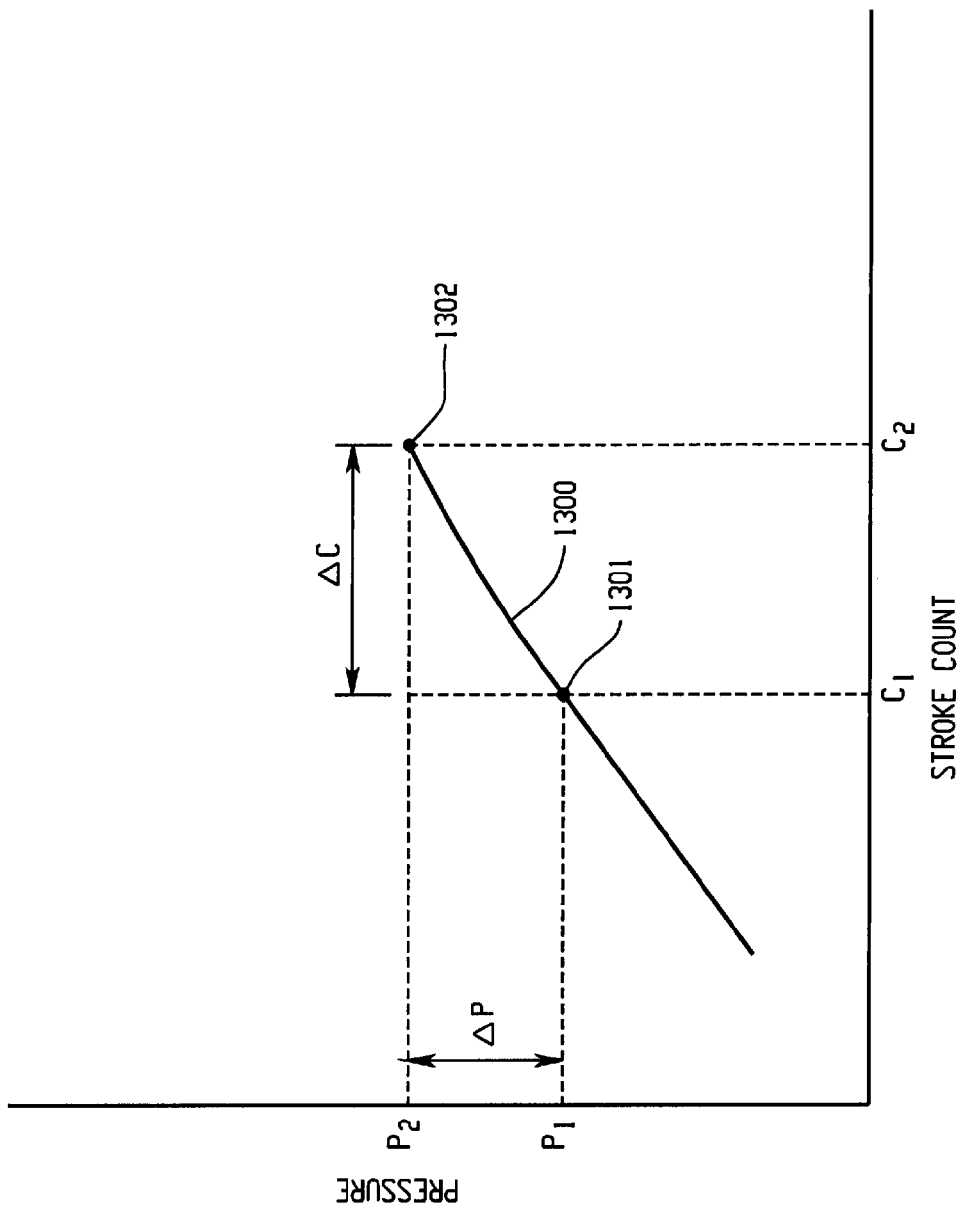
FIG. 13 is a graph that illustrates how the computer determines when to issue warning indications.

FIG. 13 illustrates how alarm (warning) conditions are determined by the computer. The line 1300 in FIG. 13 is a plot of pressure vs. strokes in accordance with graph 1230 shown in FIG. 12. The x axis parameter is strokes, and the y axis parameter is pressure. That is because strokes are a known parameter (commonly called "independent variable") that is applied in a controlled manner, whereas pressure is a parameter that is a consequence and function of the applied parameter (commonly called "dependent variable).

The two most recently collected data points 1301, 1302 are respectively taken at pressures P1 and P2. The difference between them is a value ΔP (10 psi in this case) that the user entered in the Stroke Rate field 510 (FIG. 5). Their respective stroke counts are C1 and C2, which differ by ΔC. Each time a new data point of the most recent data set is collected and graphed, the computer determines the ΔC value and compares it to both a lower preset threshold stroke value and a higher preset threshold stroke value. As long as ΔC is lower than the lower threshold, the background of "Pump Contact" 1270 is green. When ΔC is between the lower and higher thresholds, the background of "Pump Contact" 1270 is yellow. As soon as ΔC exceeds the higher threshold, the background of "Pump Contact" 1270 turns red. In this example, the higher threshold is entered by the user in the "Double Stroke" field 1260 of the "Stroke Count" tab screen 1200 of FIG. 12. The computer calculates the lower threshold as 75% of the higher threshold value.

Figure 14:
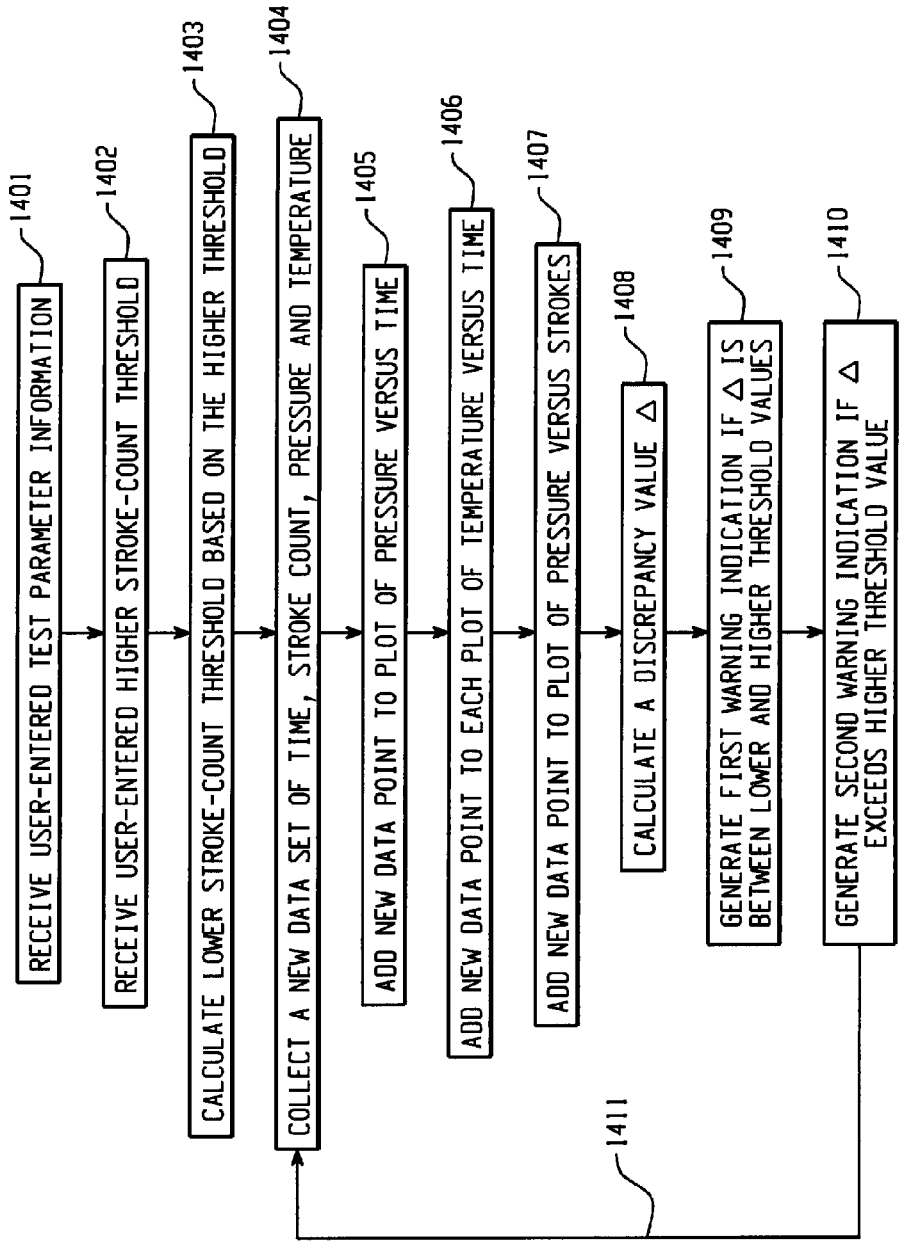
FIG. 14 is a flow chart for a method of using the test apparatus.

FIG. 14 is a flow diagram of a possible method of operation for the test apparatus 14. The computer processor receives user-entered test parameter information in step 1401. The processor receives a user-entered higher stroke-count threshold in step 1402. In step 1403, the processor calculates a lower stroke-count threshold based on the higher threshold. In step 1404, the processor collects a new data set. Each data set can include a time, a total strokes count, a pressure, and two temperatures. In steps 1405-1407, the processor adds a new data point to each plot of pressure vs. time, temperature vs. time, and pressure vs. stroke count and to a running data table.

In step 1408, the processor calculates the difference value Δ. The difference value Δ can be the difference, in stroke counts, between the stroke count of the most recent (last-collected) data point of the actual vessel plot and the stroke count of a point on an ideal vessel plot at the same pressure as that of the most recent data point. In step 1409, the processor generates a first warning indication if the discrepancy value is between the lower and higher threshold values. In step 1410, the processor generates a second, different, warning indication if the discrepancy value exceeds the higher threshold value. In step 1411, the processor returns to step 1404 to collect a new data set.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have elements that do not differ from the literal language of the claims, or if they include equivalent structural elements with insubstantial differences from the literal language of the claims.

For example, in the above procedure, the volume of media that is injected into the pipe is represented by stroke count. Alternatively, the volume injected can be measured by a measuring device that measures the injected liquid volume using another means. For example, the measurement device can include a flow rate sensor that measures flow rate in units of volume per time such as gallons per minute, and a processor that mathematically converts (such as by integration or summation) the measured flow rate to accumulated volume. Alternatively, the measurement device can include a meter that counts unit volumes (such as gallons) of the liquid directly and outputs accumulated volume, such as in gallons. In such a case, the graph 1230 (FIG. 12) of pressure would be against injected volume instead of strokes.

In the above procedure, the higher threshold is manually entered in the "Double Stroke" field 1260 (FIG. 12), against which the most recent ΔC value (i.e., the difference between the most recently collected consecutive data points) is compared for triggering an alarm. Alternatively, the threshold might be determined automatically by the computer itself based on previously collected data points. For example, the threshold can be a function of a nominally "ideal" ΔC value. The function can be a multiple of, for example twice, the nominally "ideal" ΔC value. And the "ideal" ΔC can be based on, such as equal to, the ΔC value between previously collected consecutive data points that were collected soon after the test started, when the pressure was sufficiently low that the pipe wall had not reached its plastic limit.

The shape of the curve (FIG. 13) might be mathematically processed by the computer to ascertain whether the source of the failure is due to a leak or due to pipe deformation. Or if due to both causes, to calculate a weighting factor for each of these causes of failure.

The invention claimed is:

1. A portable test apparatus for performing a pressure test on a vessel, in which, during the test, an additional amount of liquid is forced into the vessel by each successive stroke of a pump, the test apparatus comprising:
   a pressure sensor configured to measure pressure in the vessel;
   a data storage medium;
   a processor configured to monitor and store, during the test, stroke count of the pump and the pressure sensed by the pressure sensor;
   a graphical user interface comprising
   input fields to receive user-input of test parameter information; and
   a graphical representation of the stroke count and the pressure in real time that are collected during the test;
   wherein the processor is configured to collect successive data sets at a constant predetermined interval of increasing pressure, each data set including a stroke count and a pressure value at that stroke count, and upon collection of each successive data set to:
   determine a difference between the stroke count of the current data set and the stroke count of a previous data set, calculated as the stroke count of the current data set minus the stroke count of the previous data set; and
   generate a warning, indicative of a breach in the vessel, if the difference exceeds a predetermined threshold.

2. The test apparatus of claim 1, wherein the stroke count and pressure are secured from modification by a user during the test.

3. The test apparatus of claim 1, wherein the user-inputted test parameter information includes elevations relative to sea level at different locations along vessel.

4. The test apparatus of claim 1, further comprising temperature sensors for respectively measuring pipe temperature and ambient temperature, and wherein the processor is configured to monitor and store, during the test, both measured temperatures.

5. The test apparatus of claim 4, wherein the processor is further configured to plot, in real time, both the pressure and both temperatures verses time of day.

6. The test apparatus of claim 1, wherein the processor is configured to plot, during the test, the pressure vs. time and the pressure vs. stroke count.

7. The test apparatus of claim 1, wherein the predetermined threshold is a first predetermined threshold, the alarm is a first alarm, and the processor is configured to generate a second alarm, different than the first alarm, if the difference exceeds a second predetermined threshold.

8. The test apparatus of claim 7, wherein the processor is configured to input the second threshold from a user and to calculate the first threshold based on the second threshold.

9. The test apparatus of claim 1, wherein the processor is configured to determine the predetermined threshold based on a difference between pressure values of two data sets that were collected some time before the collection of the most recently collected two data sets.

10. The test apparatus of claim 1, wherein the vessel is a pipe.

11. The test apparatus of claim 1, wherein the processor is configured to input a first elevation of the vessel and a pressure of the vessel at that elevation, and to calculate, from the inputted elevation and pressure, pressures of the vessel at other elevations of the vessel.

12. The test apparatus of claim 1, wherein the processor saves on an electronic data storage medium a secure electronic report of said test parameter information and the stroke counts and the pressure collected during the test.

13. The test apparatus of claim 1, wherein the processor is configured to mathematically process the stroke count and pressure values to ascertain whether the source of the failure is due to a leak or due to wall deformation of the vessel.

14. A method for performing a pressure test on a vessel, in which, during the test, an additional amount of liquid is forced into the vessel by each successive stroke of a pump to increase the internal pressure of the vessel, the method comprising:
   inputting a user entered greater threshold;
   calculating a lesser threshold from the greater threshold;

inputting an elevation of the vessel and a pressure of the vessel at that elevation;

calculating, from the inputted elevation and pressure, pressures of the vessel at other elevations of the vessel;

collecting successive data sets at a constant predetermined interval of increasing pressure, each data set including a stroke count of the pump, the internal pressure of the vessel, a vessel temperature and an ambient temperature;

upon collecting each successive data set:

recording the most recently collected data set;

adding a data point, corresponding to the most recently collected data set, to a plot of vessel temperature versus time of day;

adding a data point, corresponding to the most recently collected data set, to a plot of ambient temperature versus time of day;

adding a data point, corresponding to the most recently collected data set, to a plot of vessel pressure versus time of day;

adding a data point, corresponding to the most recently collected data set, to a plot of vessel pressure versus stroke count;

determining a difference between a stroke count of a most recently collected data set and a previously collected data set, calculated as the stroke count of the current data set minus the stroke count of the previous data set; and generating a first warning, indicative of a breach in the vessel, if the difference exceeds the lower threshold;

generating a second, different, warning if the difference exceeds the higher threshold;

wherein the steps of the method are performed by one or more processors of a portable testing device.

15. The method of claim 14 wherein the vessel is a pipe.

* * * * *